(12) United States Patent
Bhattiprolu et al.

(10) Patent No.: US 10,107,769 B2
(45) Date of Patent: Oct. 23, 2018

(54) MULTIMODALITY MINERALOGY SEGMENTATION SYSTEM AND METHOD

(71) Applicant: Carl Zeiss X-ray Microscopy Inc., Pleasanton, CA (US)

(72) Inventors: Sreenivas Naga Bhattiprolu, Dublin, CA (US); Tom Waite, El Sobrante, CA (US)

(73) Assignee: CARL ZEISS X-RAY MICROSCOPY INC., Pleasanton, CA (US)

( * ) Notice: Subject to any disclaimer, the term of this patent is extended or adjusted under 35 U.S.C. 154(b) by 0 days.

(21) Appl. No.: 14/992,367

(22) Filed: Jan. 11, 2016

(65) Prior Publication Data

US 2017/0200290 A1  Jul. 13, 2017

(51) Int. Cl.
*G01N 23/046* (2018.01)
*G01N 23/22* (2018.01)
(Continued)

(52) U.S. Cl.
CPC .......... *G01N 23/22* (2013.01); *G01N 23/046* (2013.01); *G01V 5/00* (2013.01); *G06K 9/00664* (2013.01);
(Continued)

(58) Field of Classification Search
CPC ... C01P 2004/03; C01P 2002/85; H01J 37/28; H01J 37/26; H01J 2237/2817; G06F 17/30241; G01N 2223/616; G01N 23/046; G01N 23/223; G01N 33/24; G01N 2223/419; G01N 23/2076; G01N 2223/402
See application file for complete search history.

(56) References Cited

U.S. PATENT DOCUMENTS 7,869,565 B2   1/2011   Wood et al.
8,854,430 B2   10/2014  Varslot et al.
(Continued)

OTHER PUBLICATIONS

Igor et al., Segmentation of 3D Image of a Rock Sample Supervised by 2D Mineralogical Image, Nov. 3-6, 2015 [retrieved Apr. 28, 2017], 2015 3rd IAPR Asian Conference on Pattern Recognition, pp. 346-350. Retrieved from the Internet: http://ieeexplore.ieee.org/document/7486523/.*

(Continued)

*Primary Examiner* — Andrew Moyer
*Assistant Examiner* — Dennis Rosario
(74) *Attorney, Agent, or Firm* — HoustonHogle LLP

(57) ABSTRACT

A multimodality imaging system and method for mineralogy segmentation is disclosed. Image datasets of the sample are generated for one or more modalities, including x-ray and focused ion beam scanning electron microscope (FIB-SEM) modalities. Mineral maps are then created using Energy Dispersive X-ray spectroscopy (EDX) from at least part of the sample covered by the image datasets. The EDX mineral maps are applied as a mask to the image datasets to identify and label regions of minerals within the sample. Feature vectors are then extracted from the labeled regions via feature generators such as Gabor filters. Finally, machine learning training and classification algorithms such as Random Forest are applied to the extracted feature vectors to construct a segmented image representation of the sample that classifies the minerals within the sample.

21 Claims, 11 Drawing Sheets

(51) Int. Cl.
| | |
|---|---|
| G06T 7/40 | (2017.01) |
| G06K 9/66 | (2006.01) |
| G06T 7/00 | (2017.01) |
| G06T 7/20 | (2017.01) |
| G06T 5/10 | (2006.01) |
| G01V 5/00 | (2006.01) |
| G06K 9/00 | (2006.01) |
| G06K 9/46 | (2006.01) |

(52) U.S. Cl.
CPC ............ *G06K 9/4619* (2013.01); *G06K 9/66* (2013.01); *G06T 5/10* (2013.01); *G06T 7/0028* (2013.01); *G06T 7/2033* (2013.01); *G06T 7/40* (2013.01); *C01P 2002/85* (2013.01); *G01N 2223/402* (2013.01); *G01N 2223/405* (2013.01); *G01N 2223/616* (2013.01); *G06K 2209/19* (2013.01); *G06T 2207/10061* (2013.01); *G06T 2207/10081* (2013.01); *G06T 2207/20081* (2013.01); *G06T 2207/20084* (2013.01); *G06T 2207/30181* (2013.01)

(56) References Cited

U.S. PATENT DOCUMENTS

| | | | |
|---|---|---|---|
| 9,122,950 | B2 | 9/2015 | Han |
| 9,201,026 | B2 * | 12/2015 | Walls ............... G01N 23/22 |
| 2012/0163688 | A1 | 6/2012 | Salazar-Tio |
| 2013/0094716 | A1 | 4/2013 | Carpio et al. |
| 2013/0308831 | A1 | 11/2013 | Dvorkin et al. |
| 2014/0072095 | A1 | 3/2014 | Feser et al. |
| 2014/0376685 | A1 | 12/2014 | Koroteev et al. |
| 2015/0262400 | A1 | 9/2015 | Howell et al. |

OTHER PUBLICATIONS

Evans et al., Quantifying mineral grain size distributions for process modelling using X-ray micro-tomography, Oct. 15, 2015 [retrieved Apr. 28, 2017], Minerals Engineering, vol. 82, pp. 78-83. Retrieved from the Internet: http://www.sciencedirect.com/science/article/pii/S0892687515001168.*

Heikkila et al., A Texture-Based Method for Modeling the Background and Detecting Moving Objects, Feb. 21, 2006 [retrieved Apr. 28, 2017], IEEE Transactions on Pattern Analysis and Machine Intelligence, vol. 28, Issue: 4, pp. 657-662. Retrieved from the Internet: http://ieeexplore.ieee.org/document/1597122/#full-text-section.*

Zhang et al., Local Gabor Binary Pattern Histogram Sequence (LGBPHS): A Novel Non-Statistical Model for Face Representation and Recognition, Oct. 17-21, 2005 [retrieved Apr. 28, 2017], 10th International Conference on Computer Vision, vol. 1, 6 total pages. Retrieved from the Internet: http://ieeexplore.ieee.org/xpls/icp.jsp?arnumber=1541333&tag=1.*

Anovitz et al., Characterization and Analysis of Porosity and Pore Structures, Reviews in Mineralogy & Geochemistry, 2015 [retrieved Dec. 12, 2017], vol. 80,pp. 61-164. Retrieved from the Internet: https://www.degruyter.com/downloadpdf/books/9781501502071/9781501502071-004/9781501502071-004.pdf.*

Landrot et al., Measurement of accessible reative surface area in a sandstone, with application to $CO_2$ mineralization, Jul. 15, 2012 [retrieved Dec. 14, 2017], Chemical Geology, vol. 318-319,pp. 113-125. Retrieved from the Internet: https://www.sciencedirect.com/science/article/pii/S000925411200229X.*

Liao et al., Dominant Local Binary Patterns for Texture Classification, May 2009 [retrieved Dec. 14, 2017], IEEE Transactions on Image Processing, vol. 18, Issue:5, pp. 1107-1118.Retrieved from the Internet: http://ieeexplore.ieee.org/abstract/document/4808422/.*

Martins et al., Phase Classification by Mean Shift Clustering of Multispectral Materials Images, 2013 [retrieved Aug. 22, 2018], Microscopy and Microanalysis,pp. 1-10. Retrieved from the Internet: http://www2.famaf.unc.edu.ar/~gcas/papers/MAM13-firstview.pdf.*

Baykan, N. et al., "Mineral identification using color spaces and artificial neural networks," Computers and Geosciences, vol. 36, No. 1, 2010, pp. 91-97. Seven pages.

International Search Report and Written Opinion of the International Searching Authority, dated Sep. 23, 2016, from International Application No. PCT/US2016/012864, filed on Jan. 11, 2016. Seventeen pages.

Nielsen, A. et al., "Semi-Automatic Supervised Classification of Minerals From X-Ray Mapping Images," Proceedings of the Fourth Annual Conference of the International Association for Mathematical Geology, 1998, pp. 473-478. Six pages.

Perez, C. et al., "Rock lithological classification using multi-scale Gabor features from sub-images, and voting with rock contour information," International Journal of Mineral Processing, vol. 144, 2015, pp. 56-64. Nine pages.

International Preliminary Report on Patentability, dated Jul. 26, 2018, from International Application No. PCT/US2016/012864, filed on Jan. 11, 2016. 12 pages.

* cited by examiner

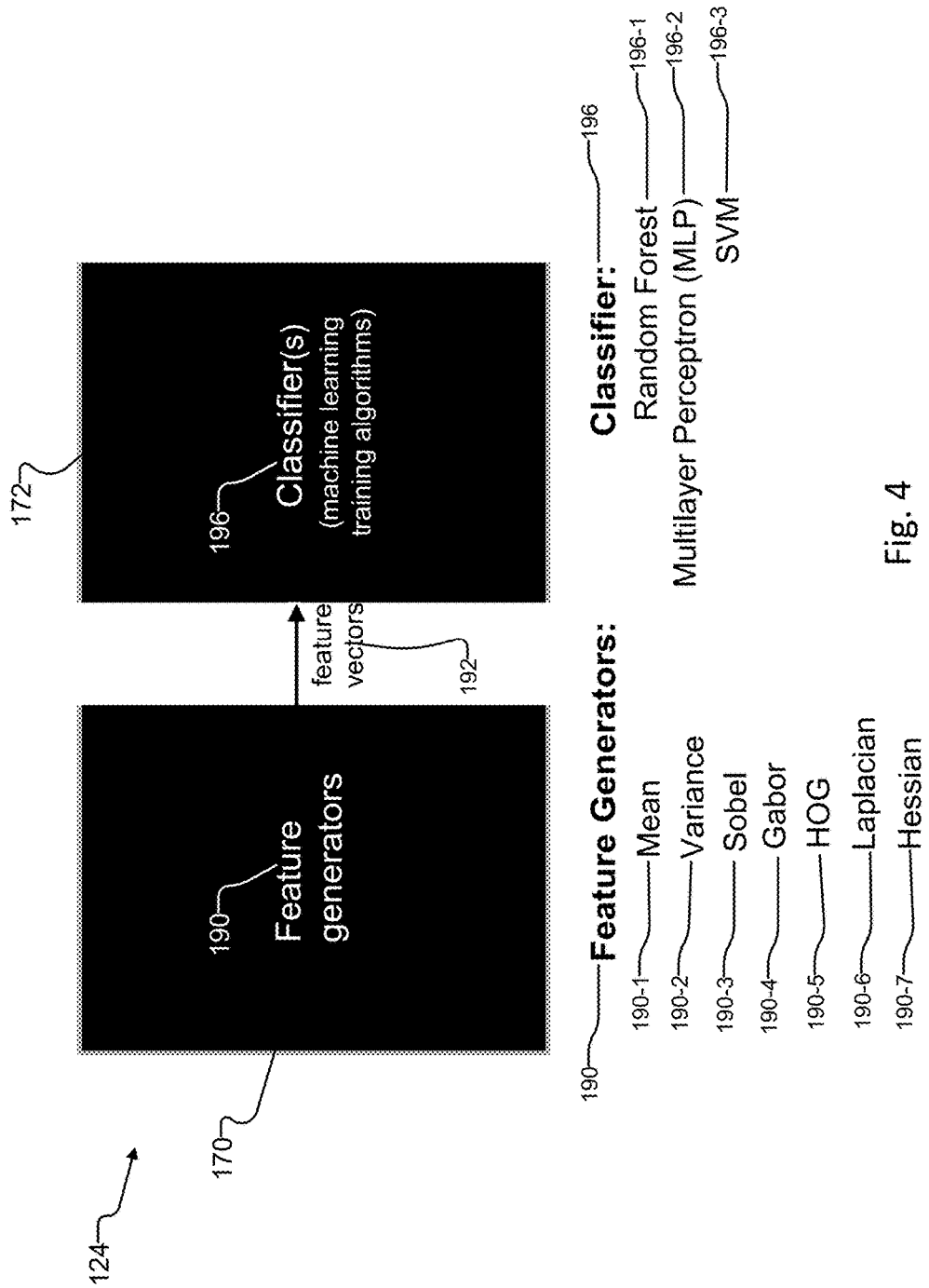

MULTIMODALITY MINERALOGY SEGMENTATION SYSTEM AND METHOD

BACKGROUND OF THE INVENTION

Various imaging modalities have been used to identify and visualize mineral content of rocks, both in two dimensions (2D) and in three dimensions (3D). For example, these imaging modalities can analyze rock samples from oil and gas extraction operations to determine porosity and mineralogy to model flow and mechanical characteristics of the samples obtained during exploration and production operations. Generally, these imaging modalities are characterized as destructive and non-destructive techniques. Further, some modalities only analyze surface features, whereas others can analyze three-dimensional structure.

In typical operation, these imaging modalities create image datasets such as 3D volumes or 2D images. Image analysis techniques are then employed to infer mineral content from the volumes and the images created by the different imaging modalities.

Non-destructive imaging systems include x-ray computed tomography (CT) microscopy and Scanning Electron Microscopy (SEM) systems. These systems provide the ability to visualize features such as pores, organics and minerals in the samples.

The X-ray CT microscopy systems irradiate the sample with x-rays, typically in a range between 1 and several hundred keV. 2D projection images are collected at multiple angles and a 3D volume of the sample is reconstructed from the projections. While the CT intensity correlates with mineral density, there is no direct way of identifying mineralogy on an X-ray CT microscope system.

SEM systems instead irradiate the sample surface with a beam of high energy electrons, typically between 500 eV and 30 keV. The signals derived from electron-sample interaction are used in constructing high resolution 2D images of the sample surface. This enables the simultaneous operation of SEM in multiple modes such as Back Scattered Electron (BSE), Secondary Electron (SE), Energy Dispersive X-ray (EDX), and Cathodoluminescence (CL) modes. EDX is typically the primary system on a SEM that offers quantitative mineralogy information which enables 2D mineral mapping of the sample surface.

Destructive imaging systems include Focused Ion Beam Scanning Electron Microscope (FIB-SEM) systems. A FIB-SEM is a multiple beam system that integrates ion beam and electron beam systems. FIB system irradiates the sample with a focused high-current beam of ions of a source material such as gallium to mill the sample surface with high precision. The milled surface is then imaged at high resolution using the integrated SEM system. The FIB milling and SEM imaging process is repeated until a desired volume is sampled. The SEM images from each slice are stacked to construct a 3D volume of the milled region of the sample.

One current imaging analysis technique creates a 3D mineral map of the sample by analyzing volume image datasets of a sample created from x-ray imaging systems. A total mineral content of the sample is then defined, and x-ray attenuation coefficients are calculated for the defined minerals. The technique then segments the grey scale 3D images by identifying characteristic grey scale levels in the images corresponding to the calculated x-ray attenuation coefficients.

Another imaging analysis technique employs multi-phase segmentation of 3D x-ray tomography volume image datasets. The 3D x-ray tomography volumes are processed to obtain a standardized intensity grey scale images, which are then segmented into at least 3 phases. The segmentation steps include computing a median/mean-filtered-gradient image of the standardized intensity image, creating an intensity vs. gradient graph from the median/mean-filtered-gradient image and the standardized intensity image, partitioning the intensity vs. gradient graph into at least 3 regions, and using thresholds defining the regions to segment the standardized grey scale image to create the segmented image. Then, volumetric fractions and spatial distributions of the segmented phases are calculated and compared with target values.

SUMMARY OF THE INVENTION

Current imaging and mineral assignment techniques have limitations. For example, the technique associated with 3D mineral map creation cannot distinguish between minerals with overlapping CT values. This can occur when clusters of grains include minerals that are very close in average atomic number. In addition, the technique can assign the wrong mineralogy to voxels/pixels located on the edges or boundaries of areas within the images. On the other hand, multi-phase segmentation methods can be complicated, computationally intensive, and suffer from the same issues as the 3D mineral map imaging analysis technique.

In general, according to one aspect, the invention features a mineralogy segmentation method for a multimodality imaging system. The method comprises generating one or more image datasets of a sample, creating one or more mineral maps covering at least part of the one or more image datasets, and applying the one or more mineral maps as a mask to the one or more image datasets to identify and label regions associated with minerals within the sample. The one or more image datasets are generated using different imaging modalities of the multimodality imaging system. Then, feature vectors are extracted from the labeled regions via feature generators and machine learning training algorithms are executed upon the extracted feature vectors to learn behavior information of the feature vectors. This behavior information learned from the machine learning training algorithms is then applied to the one or more image dataset to construct a segmented image representation of the sample that classifies the minerals within the sample.

In one example, labeled images are converted to a set of feature vectors via feature generators. One such feature generator is a Gabor filter that is used for texture and edge extraction. Gabor filters are primarily characterized by three parameters: wavelength, angle, and bandwidth. Multiple Gabor feature generators can be built by varying these parameters. The application of feature generators on the labeled images result in images where each pixel is represented by a feature vector that is an array of points in vector space. Minerals with unique texture in the image datasets will cause unique feature vectors to be generated that represent corresponding minerals, in one example.

In this example, machine learning training algorithms are then executed upon the extracted feature vectors to associate certain values of feature vector combinations of features with the corresponding mineral phase. One such machine learning training algorithm is Random Forest which is an ensemble learning method that constructs multiple decision trees during training. Each decision tree is constructed by using a random subset of training data. The decision tree information from the labeled images is then applied to the one or more unlabeled image datasets to construct a segmented image representation of the sample that classifies the minerals within the sample.

Another exemplary machine learning training algorithm is Multilayer Perceptron (MLP) that draws decision boundaries between classes. MLP is a function mapping classifier that solves equation Y=F(x), where x is the feature vector, Y is the class and F is the learned function that generates decision boundaries. The decision boundaries are defined for one or more unlabeled image datasets to construct a segmented image representation of the sample that classifies the minerals within the sample.

In embodiments, the mineral maps are created using energy dispersive x-ray spectroscopy to identify the minerals within the sample. Further, generating the one or more image datasets of the sample can comprise generating one or more x-ray volume datasets of the sample as the one or more image datasets. These can include one or more x-ray volume datasets of the sample using different x-ray energies.

Further, the generation of the one or more image datasets of the sample can comprise generating one or more FIB-SEM volume datasets of the sample as one or more image datasets using a focused ion beam scanning electron microscope (FIB-SEM) imaging and analysis system of the multimodality imaging system. Backscattered electron and/or secondary electron modes of the FIB-SEM imaging and analysis system can be used.

In one case, at least one of the image datasets is a FIB-SEM volume dataset and the segmented image representation of the sample is a segmented FIB-SEM volume dataset.

In another case, the at least one of one or more image datasets of the sample includes one or more FIB-SEM datasets of the sample as one or more image datasets using a focused ion beam scanning electron microscope (FIB-SEM) imaging and analysis system of the multimodality imaging system.

In general, according to another aspect, the invention features a multimodality imaging system for segmenting minerals of a sample. This system comprises an imaging system generating one or more image datasets of the sample and an energy dispersive x-ray spectroscopy system creating one or more mineral maps that identify the minerals within the sample. A computer system applies the one or more mineral maps as a mask to the one or more image datasets to identify and label regions associated with the minerals within the sample. A feature extraction engine is utilized that extracts feature vectors from the labeled regions. A machine learning engine is also utilized that executes machine learning training algorithms upon the extracted feature vectors to learn behavior information of the feature vectors. Finally, the behavior information learned from the machine learning training algorithms are applied to the one or more image datasets to construct a segmented image representation of the sample that classifies the minerals within the sample.

Exemplary applications for the invention include the analysis of samples from materials science and geosciences. The present invention can be used to construct segmented image representations of samples such as Solid Oxide Fuel Cells (SOFC) and meteorites, in examples. The segmented image representations classify phases and minerals within the samples with improved image resolution and with improved operational efficiency as compared to current systems and methods.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 4 is a schematic block diagram that shows relationships between different collaborative processes/applications executing on a computer system of the multimodality imaging system, where the processes include a feature extraction engine and a machine learning engine that operate upon the image datasets of the sample in the embodiments of FIG. 3A-3C to construct associated segmented image representations of the sample;

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Figure 1:
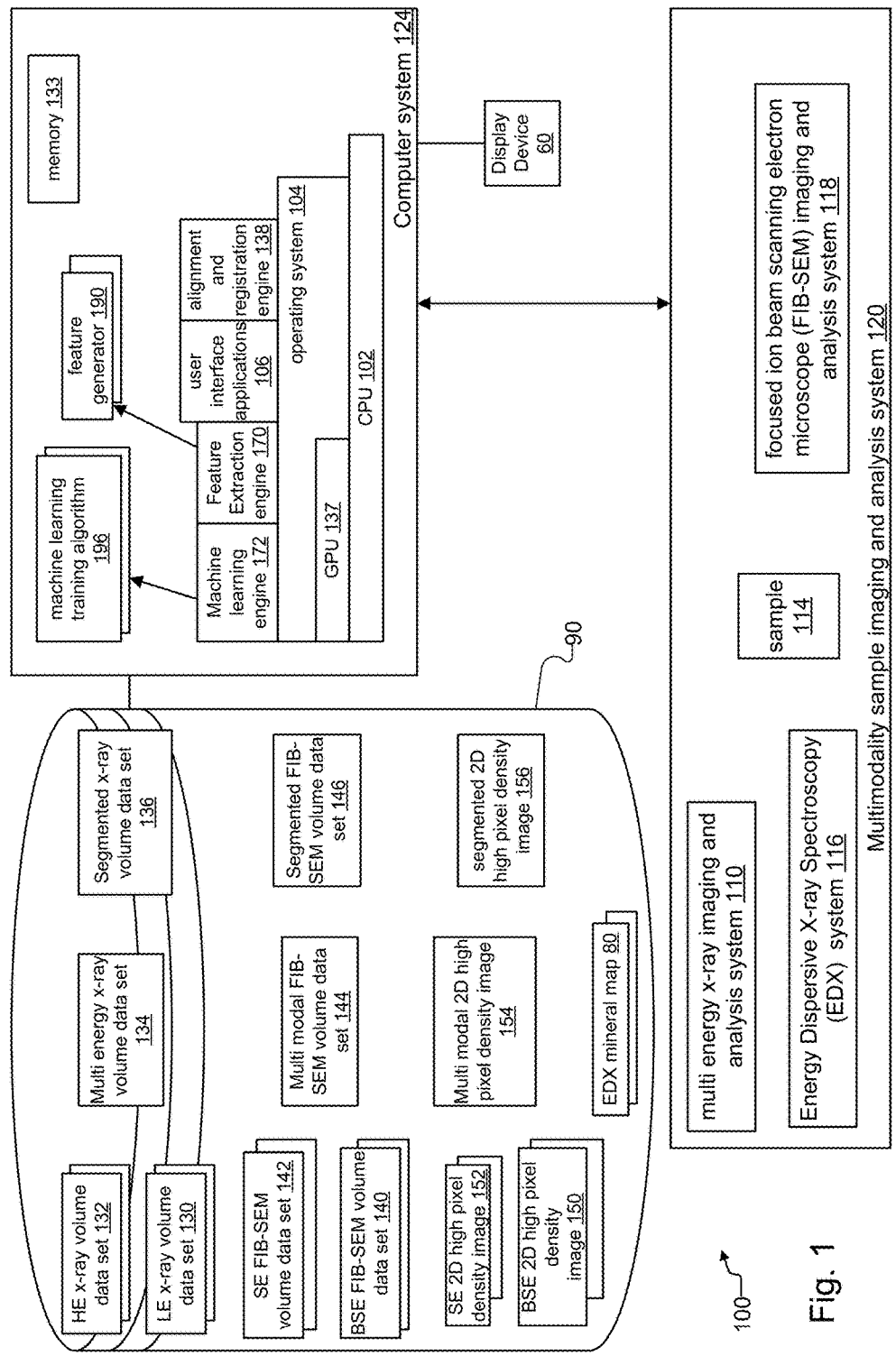
FIG. 1 is a system block diagram that shows the major components of a multimodality imaging system for determining mineralogy of a sample.

FIG. 1 shows an exemplary multi-modality imaging system 100. The system 100 includes a datastore 90, a computer system 124, and a multi-modality sample imaging and analysis system 120. The system 100 is utilized to classify (e.g. segment and label) regions of minerals within samples 114 and characterize microstructures within the samples 114.

The multi-modality sample imaging and analysis system 120 includes subsystems associated with different imaging modalities. These include a multi energy x-ray imaging and analysis system 110, a focused ion beam scanning electron microscope (FIB-SEM) imaging and analysis system 118, and an Energy Dispersive X-ray Spectroscopy (EDX) system 116. The multi-modality sample imaging and analysis system 120 in conjunction with the computer system 124 generate image datasets of the sample 114. The image datasets are saved to the datastore 90.

The computer system 124 includes one or more hardware-based central processing units (CPU) 102, one or more graphical processing units (GPUs) 137 and physical memory 133. The computer system 124 also includes an operating system 104 that executes on the CPU(s) 102 and can optionally communicate with the GPU 137.

One or more applications or processes execute on the operating system 104 within one or more contexts as determined by the operating system 104. The applications include a machine learning engine 172, a feature extraction engine 170, user interface applications 106 and an alignment and registration engine 138. In examples, the applications are proprietary and/or standardized graphics applications that present application programming interfaces (APIs). The APIs presented by the applications enable cooperative communications and processing between the operating system 104, CPU 102, and GPU 137 via memory 133 and communications buses, in examples.

The computer system 124 also includes machine learning training algorithms 196 and feature generators 190. The feature extraction engine 170 uses the feature generators 190 to extract feature vectors 192 from image datasets. The machine learning engine 172 applies the machine leaning training algorithms 196 to the extracted feature vectors 192.

It can be appreciated that applications such as the machine learning engine 172 and the feature extraction engine 170 can also be implemented in hardware such as within the GPU 137. Moreover, the capabilities of the machine learning engine 172 and the feature extraction engine 170 can be combined into a common process or hardware component, in other implementations.

Operators utilize the user interface applications 136 to interact with the major components of the multi-modality imaging system 100 such as the computer system 124, the multi-modality sample imaging and analysis system 120, and the datastore 90. A display device 60 connected to the computer system 124 allows the operator to execute tasks upon the components and display results.

The x-ray imaging and analysis system 110 uses x-rays and possibly x-rays at different energies to generate one or more x-ray volume datasets of the sample 114 as the image datasets. The imaging typically operate across the 3D volume of the sample 114. In one embodiment, the imaging includes low energy (LE) dataset that typically uses x-rays below 70 keV, and high energy (HE) dataset that typically uses x-rays above 100 keV, in examples. The LE datasets create LE x-ray volume datasets 130 and HE datasets create HE x-ray volume datasets 132. The alignment and registration engine 138 of the computer system 124 then aligns and registers the LE and HE volume datasets 130/132 with each other to create a multi energy x-ray volume dataset 134 and saves it to the datastore 90.

The FIB-SEM imaging and analysis system 118 enables creation of Secondary Electron (SE) and/or Back Scattered Electron (BSE) image datasets of the sample 114. In one embodiment, an operator can use the FIB-SEM imaging and analysis system 118 to scan across the entirety of the sample 114 to create BSE and SE FIB-SEM volume datasets 140/142 of the sample 114. The alignment and registration engine 138 aligns and registers the BSE and SE FIB-SEM volume datasets 140/142 with each other to create a multi modal FIB-SEM volume dataset 144 and saves it to the datastore 90.

In yet another embodiment, an operator can use the FIB-SEM imaging and analysis system 118 to create BSE and SE 2D high pixel density images 150/152 of the surface of the sample 114 as the image datasets. In contrast to the BSE and SE FIB-SEM volume datasets 140/142, the BSE and SE 2D high pixel density images 150/152 are scanned over a much larger region at high resolution. The EDX system 116 also typically operates at slower rates compared to the BSE and SE imaging speeds of the FIB-SEM imaging and analysis system 118. For these reasons, the EDX mineral maps 80 are created by limiting the scan to a specific area or cross-section of the sample 114. The alignment and registration engine 138 aligns and registers the BSE and SE 2D high pixel density images 150/152 with each other to create a multi modal 2D high pixel density image 154 and saves it to the datastore 90.

The system 100 uses the EDX system 116 of the Multi-modality sample imaging and analysis system 120 to create one or more EDX mineral maps 80 of the sample 114. EDX mineral maps 80 are 2D images of selected slices of the sample 114. The EDX mineral maps 80 are generated by utilizing the characteristic spectra of elements within the sample 114 and identifying mineralogy at every pixel for the selected slice. The EDX mineral maps 80 establish a "ground truth" of the mineralogy of the analyzed surface within the sample 114 volume.

Preferably, the slices of the sample 114 selected for creation of the EDX mineral maps 80 include one or more 2D slices or surfaces of the sample 114 that are at least also covered by the image datasets of the sample 114 associated with each of the embodiments/imaging modalities. For the embodiment associated with the x-ray modality, the EDX mineral maps 80 are preferably created from one or more 2D slices or sample surfaces covered by the multi energy x-ray volume dataset 134. For the embodiment associated with creation of the BSE and SE FIB-SEM volume datasets, the EDX mineral maps 80 are created from one or more 2D slices or sample surfaces covered by the multi modal FIB-SEM volume dataset 144. Typically, the at least one slice selected for creation of the EDX mineral maps 80 is from the surface of the sample 114. Finally, for the embodiment associated with creation of the multi modal 2D high pixel density image 154, the EDX mineral maps 80 are created from one or more small regions within the sample 114 that are also covered by the multi modal 2D high pixel density image 154.

Typically, the EDX mineral maps 80 are collected/generated from a surface slice of the sample 114. However, the EDX mineral maps 80 can also be created from slices or surfaces associated with selected regions of interest exposed from within the sample 114. In one example, BSE images taken of the sample 114 via the FIB-SEM imaging and analysis system 118 can assist in identifying regions of interest within the sample 114 from which the EDX mineral maps 80 can be created. The alignment and registration engine 138 aligns and registers the EDX mineral maps 80 with the multi energy x-ray volume dataset 134, the multi modal FIB-SEM volume dataset 144, and the multi modal 2D high pixel density image 154 and saves these aligned versions to the datastore 90.

The machine learning engine 172 accepts the aligned and correlated datasets 132/130, 142/140, 152/150 along with EDX mineral maps 80. In conjunction with the feature extraction engine 170, the machine learning engine 172 applies the information associated with the corresponding pixels for each mineral identified by the EDX mineral maps 80 to each of the multi energy x-ray volume dataset 134, the multi modal FIB-SEM volume dataset 144, and the multi modal 2D high pixel density image 154 to create corresponding segmented image representations of the sample 114 and saves them to the datastore 90. The corresponding segmented image representations are segmented x-ray volume datasets 136, segmented FIB-SEM volume datasets 146, and segmented 2D high pixel density images 156, respectively.

Though the disclosed embodiments of the mineralogy segmentation methods preferably accept as input either single or multi energy x-ray volume datasets 134, single or multi modal FIB-SEM volume datasets 144, or single or multi modal 2D high pixel density images 154, it can be appreciated that the segmentation methods also accepts individual datasets or multiple datasets of the same modality. The datasets are then processed into their associated segmented image representations. In one example, a single LE or HE x-ray volume dataset 130/132 can be processed to create a segmented x-ray volume dataset 136. In another example, a single BSE 2D high pixel density image 150 can be processed to create a segmented 2D high pixel density image 156. In yet another example, a BSE FIB-SEM volume dataset 142 of the sample 114 can be generated, and then processed to create a segmented FIB-SEM volume dataset 146.

Figure 2:
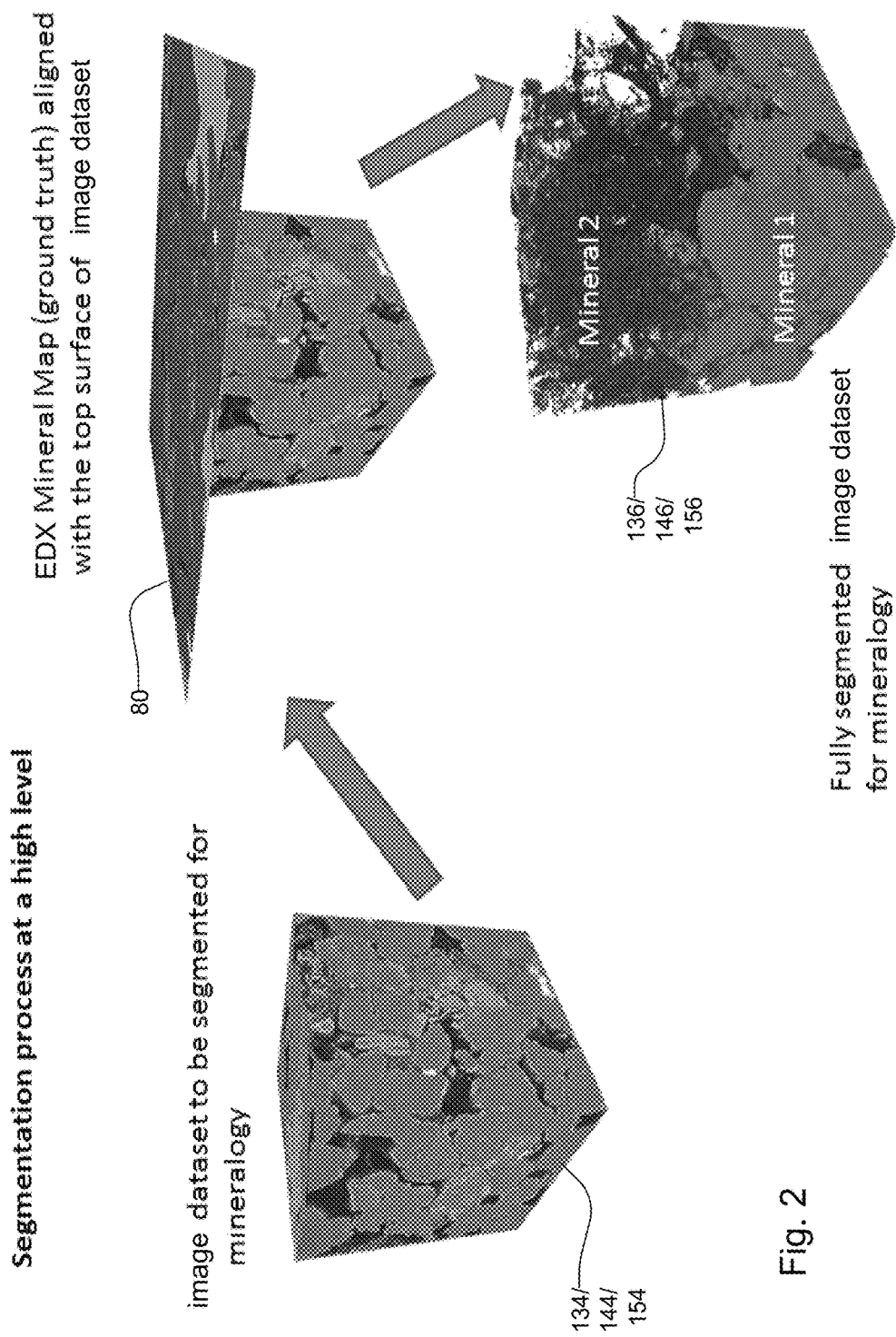
FIG. 2 is a schematic block diagram that provides a high-level description of a method for constructing segmented image representations of a sample according to concepts of the present invention.

FIG. 2 provides a high-level description of a method for constructing segmented image representations of a sample 114. Image datasets 134/144/154 of a sample 114 are created according to one or more of the imaging modalities for the sample 114. Then, an EDX mineral map 80 (ground truth) is aligned with a surface of the image dataset. Finally, the EDX mineral map 80 is applied to the image datasets 134/144/154 to create associated segmented image datasets 136/146/156 for mineralogy.

Figure 3A:
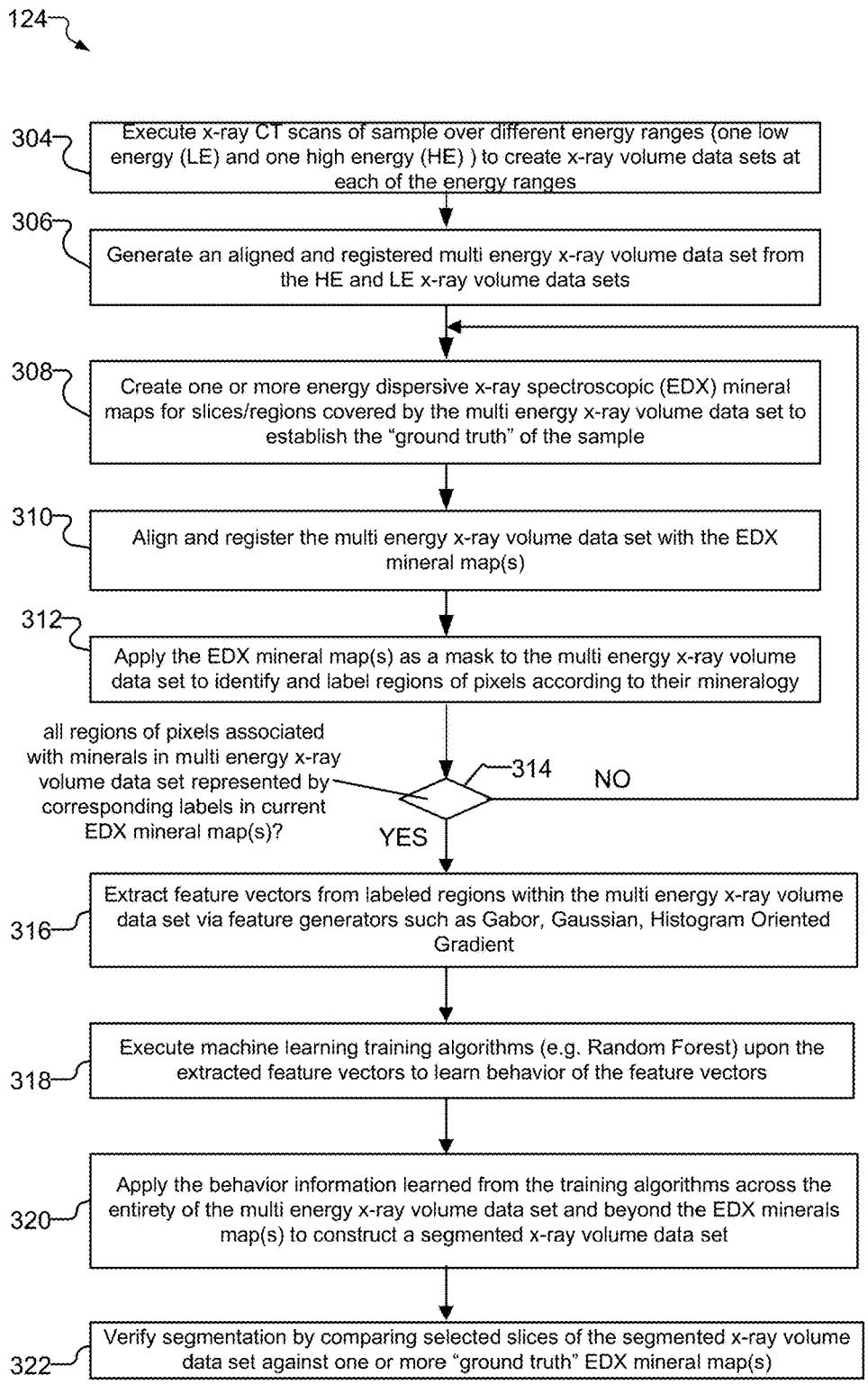
FIG. 3A-3C are flow charts that describe preferred embodiments of the invention, where each of the embodiments describes a method executed by a computer system to construct segmented image representations of the sample, with FIG. 3A describing a method for generating a segmented x-ray volume dataset of the sample, and with FIGS. 3B and 3C describing methods for generating a segmented FIB-SEM volume dataset and a segmented 2D high pixel density image of the sample, respectively.
Figure 3B:
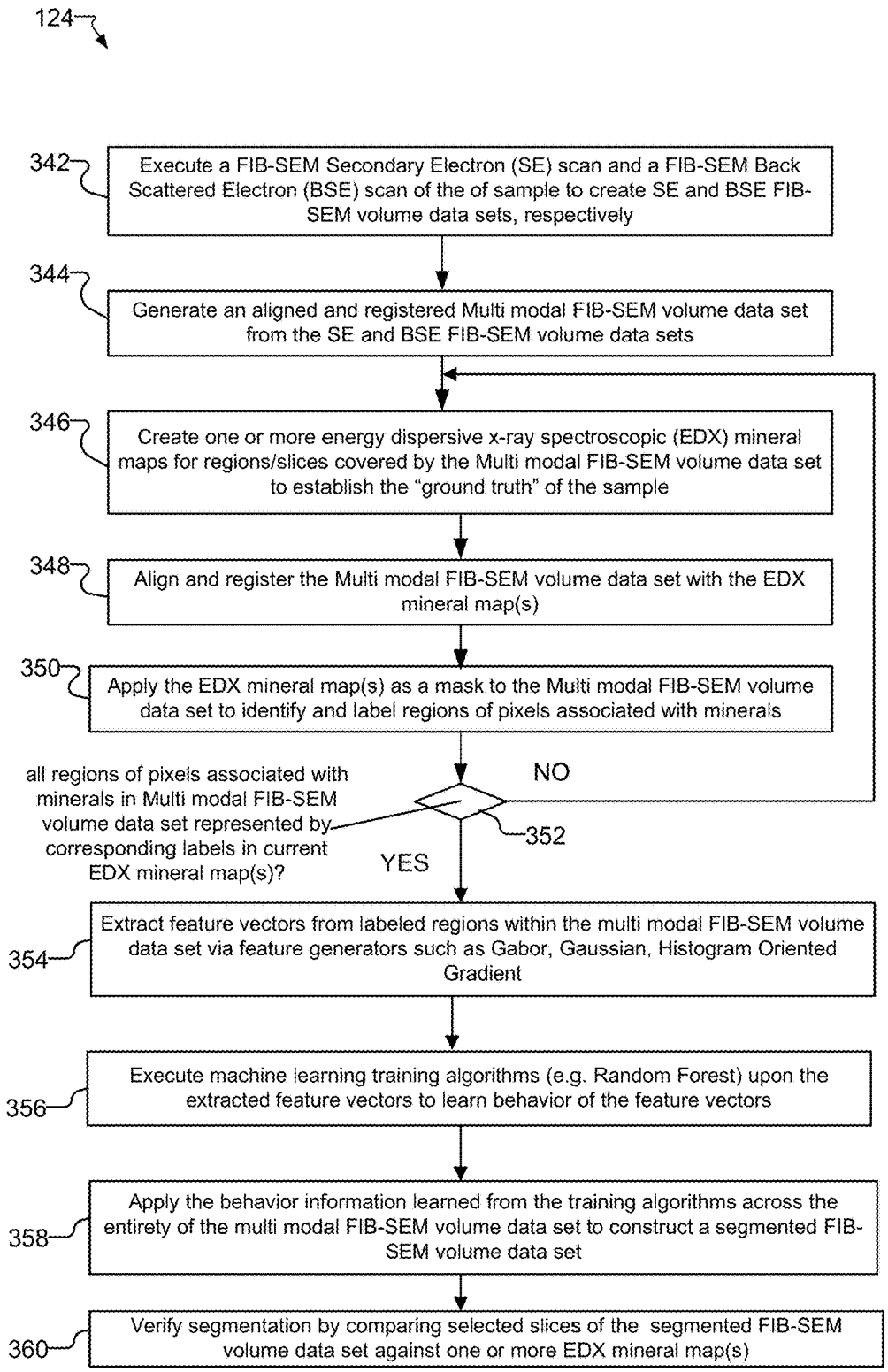
Figure 3C:
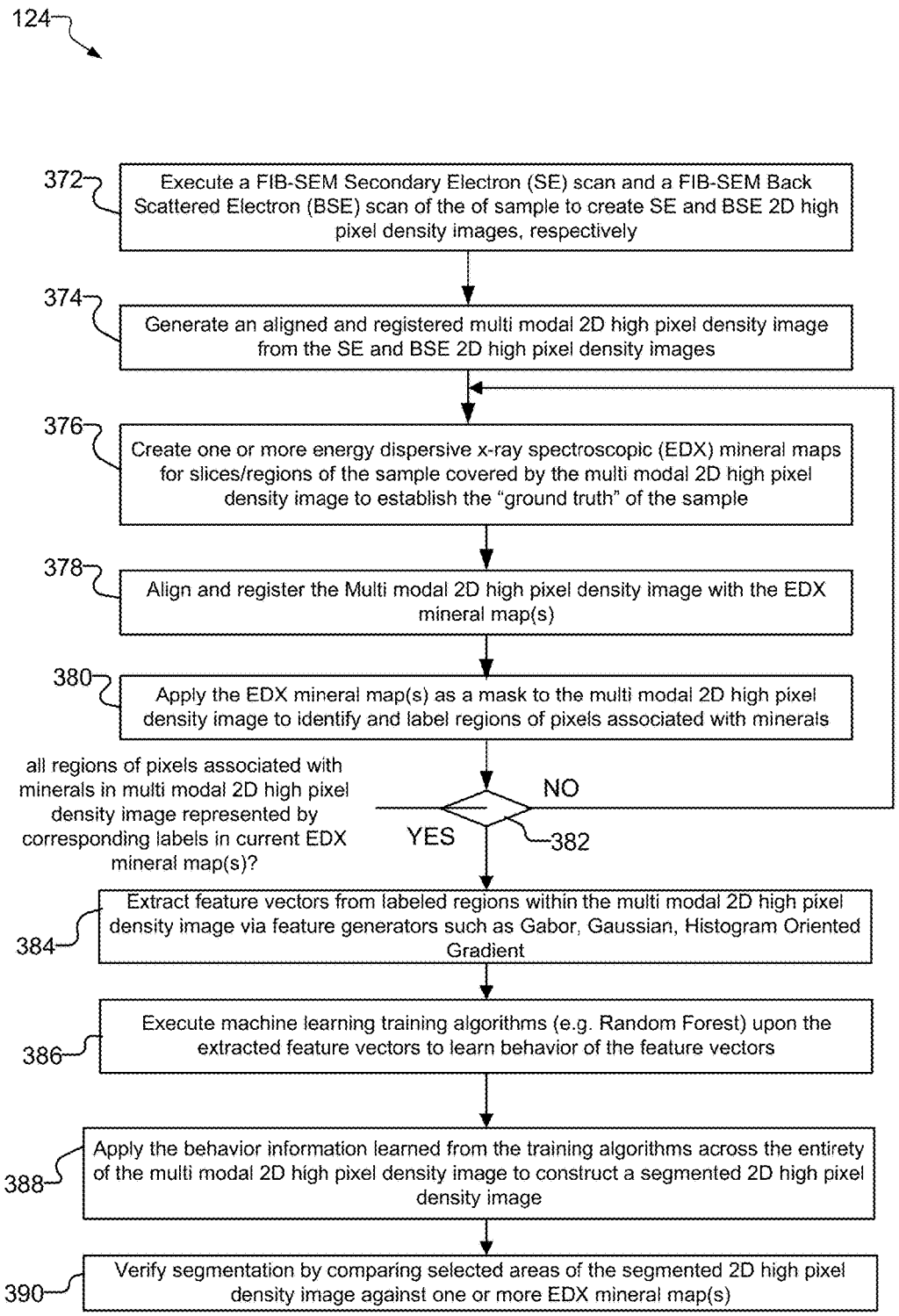

FIG. 3A-3C describe the preferred mineralogy segmentation methods executed by the computer system 124 for different imaging modalities.

FIG. 3A shows a method of the computer system 124 for generating a segmented x-ray volume dataset 136 of the sample 114 for an x-ray modality.

In step 304, the computer system 124 instructs the multi energy x-ray imaging and analysis system 110 to execute x-ray CT imaging of the sample 114 over different energy ranges (one low energy (LE) and one high energy (HE)) to create x-ray volume datasets at each of the energy ranges. LE and HE x-ray volume datasets 130/132 are created as a result of this step.

In step 306, the alignment and registration engine 138 generates an aligned and registered multi energy x-ray volume dataset 134 from the HE and LE x-ray volume datasets 132/130.

According to step 308, the computer system 124 instructs the EDX system 116 to create one or more EDX mineral maps 80 of the sample 114. The alignment and registration engine 138 aligns and registers the multi energy x-ray volume dataset 134 with the EDX mineral map(s) 80 in step 310.

In step 312, the computer system 124 applies the EDX mineral map(s) 80 as a mask to the multi energy x-ray volume dataset 134 to identify and label regions of pixels/voxels associated according to their mineralogy.

In step 314, the computer system 124 determines if all regions of pixels associated with minerals in the multi energy x-ray volume dataset 134 are represented by corresponding labels in the current EDX mineral map(s) 80. If this statement is false, control passes back to the beginning of step 308 to create additional EDX mineral maps 80. Otherwise, control passes to step 316.

In step 316, the feature extraction engine 170 extracts feature vectors 192 from labeled regions within the multi energy x-ray volume dataset 134 via feature generators 190 such as Gabor, Gaussian, and Histogram Oriented Gradient filters, in examples. According to step 318, the machine learning engine 172 executes machine learning training algorithms 196 upon the extracted feature vectors 192 to learn behavior of the feature vectors 192. An exemplary machine learning training algorithm 196 is Random Forest 196-1.

In step 320, the machine learning engine 172 preferably applies the behavior information learned from the training algorithms 196 across the entirety of the multi energy x-ray volume dataset 134 and beyond the EDX mineral map(s) 80 to construct a segmented and labeled x-ray volume dataset 136 of the sample 114. Finally, in step 322, the computer system 124 verifies the segmentation by comparing selected slices of the segmented x-ray volume dataset 136 against one or more ground truth EDX mineral maps 80.

FIG. 3B shows a method for the computer system 124 generating a segmented FIB-SEM volume dataset 146 of the sample 114 for a FIB-SEM imaging modality.

In step 342, the computer system 124 instructs the FIB-SEM imaging and analysis system 118 to execute a FIB-SEM Secondary Electron (SE) scan and/or a FIB-SEM Back Scattered Electron (BSE) scan of the of sample to create SE and/or BSE FIB-SEM volume datasets 142/140 of the sample 114, respectively.

In step 344, the alignment and registration engine 138 generates an aligned and registered multi modal FIB-SEM volume dataset 144 from the SE and/or BSE FIB-SEM volume datasets 142/140. According to step 346, the computer system 124 instructs the EDX system 116 to create one or more EDX mineral maps 80 for regions/slices covered by the FIB-SEM volume dataset 144 to establish the "ground truth" of the sample 114. The alignment and registration engine 138 aligns and registers the multi modal FIB-SEM volume dataset 144 with the EDX mineral map(s) in step 348.

In step 350, the computer system 124 applies the EDX mineral map(s) 80 as a mask to the multi modal FIB-SEM volume dataset 144 to identify and label regions of pixels associated with minerals. In step 352, the computer system determines if all regions of pixels/voxels associated with minerals in the multi modal FIB-SEM volume dataset 144 are represented by corresponding labels in the current EDX mineral map(s) 80. If this statement is false, control passes back to the beginning of step 346 to create additional EDX mineral maps 80. Otherwise, control passes to step 354.

In step 354, the feature extraction engine 170 extracts feature vectors 192 from labeled regions within the multi modal FIB-SEM volume dataset 144 via feature generators 190. According to step 356, the machine learning engine 172 executes machine learning training algorithms 196 upon the extracted feature vectors 192 to learn behavior of the feature vectors 192.

In step 358, the machine learning engine 172 preferably applies the behavior information learned from the training algorithms 196 across the entirety of the multi modal FIB-SEM volume dataset 144 to construct a segmented FIB-SEM volume dataset 146 of the sample 114. Finally, in step 360, the computer system 124 verifies the segmentation by comparing selected slices of the segmented FIB-SEM volume dataset 146 against one or more EDX mineral map(s) 80.

FIG. 3C shows a method for the computer system 124 to generate a segmented 2D high pixel density image 156 of the sample 114 for a FIB-SEM modality.

In step 372, the computer system 124 instructs the FIB-SEM imaging and analysis system 118 to execute a FIB-SEM Secondary Electron (SE) scan and/or a FIB-SEM Back Scattered Electron (BSE) scan of the of sample to create SE and BSE 2D images 152/150 of the sample 114, respectively.

In step 374, the alignment and registration engine 138 generates an aligned and registered multi modal 2D image 154 from the SE and BSE 2D images 152/150. According to step 376, the computer system 124 instructs the EDX system 116 to create one or more EDX mineral maps 80 from regions of the sample that are covered by the multi modal 2D image 154 to establish the "ground truth" of the sample 114. The alignment and registration engine 138 aligns and registers the multi modal 2D mage 154 with the EDX mineral map(s) in step 378.

In step 380, the computer system 124 applies the EDX mineral map(s) 80 as a mask to the multi modal 2D high pixel density image 154 to identify and label regions of pixels associated with minerals. In step 382, the computer system determines if all regions of pixels/voxels associated with minerals in the multi modal 2D high pixel density image 154 are represented by corresponding labels in the current EDX mineral map(s) 80. If this statement is false, control passes back to the beginning of step 376 to create additional EDX mineral maps 80. Otherwise, control passes to step 384.

In step 384, the feature extraction engine 170 extracts feature vectors 192 from labeled regions within the multi modal 2D high pixel density image 154 via feature generators 190. According to step 386, the machine learning engine 172 executes machine learning training algorithms 196 upon the extracted feature vectors 192 to learn behavior of the feature vectors 192.

In step 388, the machine learning engine 172 preferably applies the behavior information learned from the training algorithms 196 across the entirety of the multi modal 2D high pixel density image 154 to create a segmented 2D high pixel density image 156 of the sample 114. Finally, in step 390, the computer system 124 verifies the segmentation by comparing selected areas of the segmented 2D high pixel density image 156 against one or more EDX mineral map(s) 80.

FIG. 4 shows how the feature extraction engine 170 and the machine learning engine 172 of the computer system 124 operate in a collaborative fashion to construct the segmented image representations 136/146/156 of the sample 114. The feature extraction engine 170 loads the feature generators 190 from the computer system 124. The feature generators 190 include filters such as mean 190-1, variance 190-2, Sobel 190-3, Gabor 190-4, Histogram of Oriented Gradients (HOG) 190-5, Laplacian 190-6, and Hessian 190-7 filters, in examples. These filters are typically digital filters. In one example, the Gabor filter 190-4 is applied to the multi energy x-ray volume dataset 134, the multi modal FIB-SEM volume dataset 144, and the multi modal 2D high pixel density image 154 with varying angle, bandwidth, and frequency parameter values.

In response to the feature extraction engine 170 applying the feature generators 190 to an image dataset, each pixel in the image dataset is assigned an array of vector values for each feature generator 190 (e.g. filter) applied. These vector values are also known as feature vectors 192. The feature extraction engine 170 then provides the feature vectors 192 for processing by other applications that execute within the computer system 124.

The machine learning engine 172 loads the classifiers/machine learning training algorithms 196 from the computer system 124. Exemplary machine learning training algorithms include Random Forest 196-1, Multilayer Perception neural network (MLP) 196-2, and Support Vector Machine (SVM) 196-3.

The machine learning engine 172 accepts the feature vectors 192 passed by the feature extraction engine 170. The machine learning engine 172 executes the machine learning training algorithms 196 upon the feature vectors 192, and applies the information learned from this process to the entirety of the image datasets that were aligned with the EDX mineral maps 80 (e.g. the multi energy x-ray volume dataset 134, the multi modal FIB-SEM volume dataset 144, and the multi modal 2D high pixel density image 154). The constructed segmented image representations that result are the segmented x-ray energy volume dataset 136, the segmented FIB-SEM volume dataset 146, and the segmented 2D high pixel density image 156, respectively.

Figure 5:
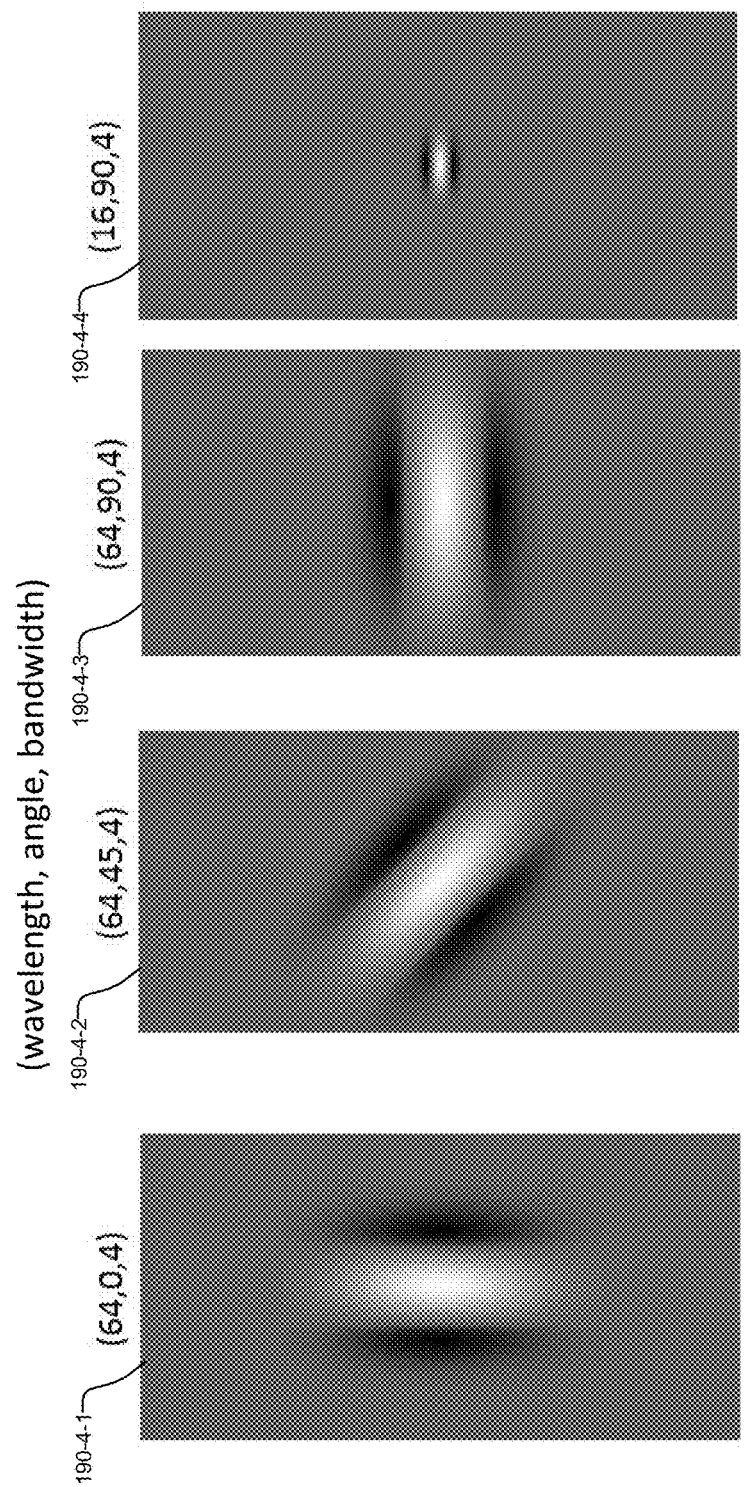
FIG. 5 shows images of different exemplary Gabor filter feature generators utilized by the feature extraction engine.

FIG. 5 shows images representing different exemplary 2D Gabor feature generators 190-4-1 through 190-4-4, each having different (wavelength, angle, bandwidth) parameter values (64, 0, 4), (64, 45, 4), (64, 90, 4) and (16, 90, 4), respectfully.

In a typical machine learning framework, a large set of feature generators 190 such as Gabor filters 190-4 are selected over a range of different wavelength, angle and bandwidth settings. Gabor filters 190-4 are complex kernels and they generate a set of filtered images. In one example, a Gabor filter 190-4 kernel has 18 frequencies and eleven angles, which creates a total of 198 images.

In response to the feature extraction engine 170 applying the Gabor filters 190-4 to an image dataset 134/144/154, feature vectors 192 are created. For the Gabor filter 190-4 example, the created feature vectors 192 are arrays of Gabor values at each pixel location in the image dataset 134/144/154.

Figure 6:
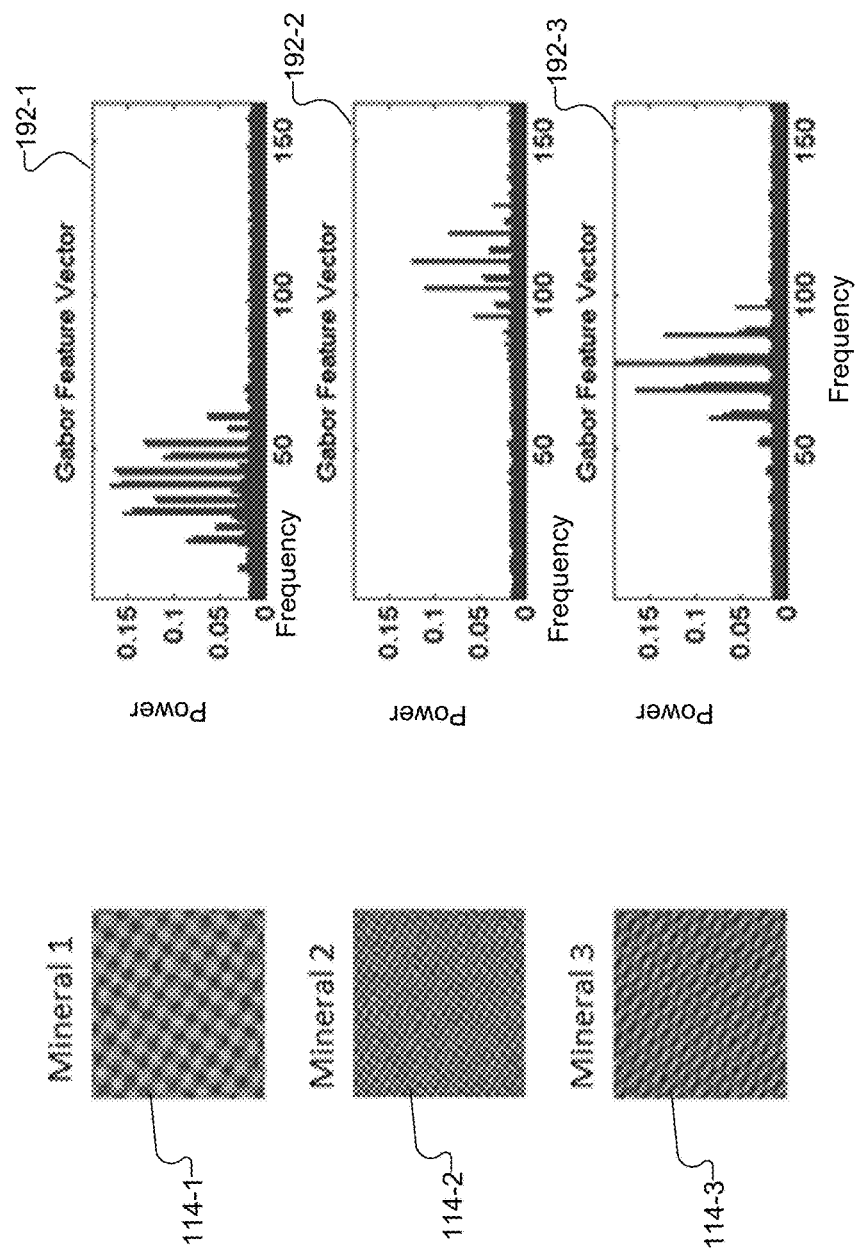
FIG. 6 shows three different image dataset snippets for samples having different mineral textures, and power versus frequency plots of associated feature vectors created for each of the samples.

FIG. 6 shows power versus frequency plots of Gabor feature vectors 192-1 through 192-3 created for three 64×64 images snippets of mineral samples 114-1 through 114-3 having different textures. Each of the plots was generated by applying Gabor feature generators 190-4 to an image dataset 134/144/154 of samples 114-1 through 114-3. For creating each of the feature vectors 192-1 through 192-3, the same Gabor feature generator 190-4 bandwidth setting was selected by the feature extraction engine 170 when applying the Gabor feature generator 190-4 to the image datasets 134/144/154.

Because Gabor feature generators 190-4 are windowed Fourier transforms, the vertical axis of each plot in the current example is power, and the x axis is a combination of angle and frequency. Moreover, because the feature vectors 192 were created by applying Gabor filter 190-4 feature generators, the feature vectors 192 are also referred to as Gabor feature vectors 192-1 through 192-3. The machine learning engine 172 "learns" the texture of each sample 114 by executing machine learning training algorithms 196 upon the generated feature vectors 192-1 through 192-3.

The differences in the power versus frequency plots of feature vectors 192-1 through 192-3 correspond to the different textures of the samples 114-1 through 114-3. In examples, the large spikes in the plots of the feature vectors 192-1 through 192-3 are narrow frequencies and angles where the power is high. The broad flat area is the background noise.

Figure 7A:
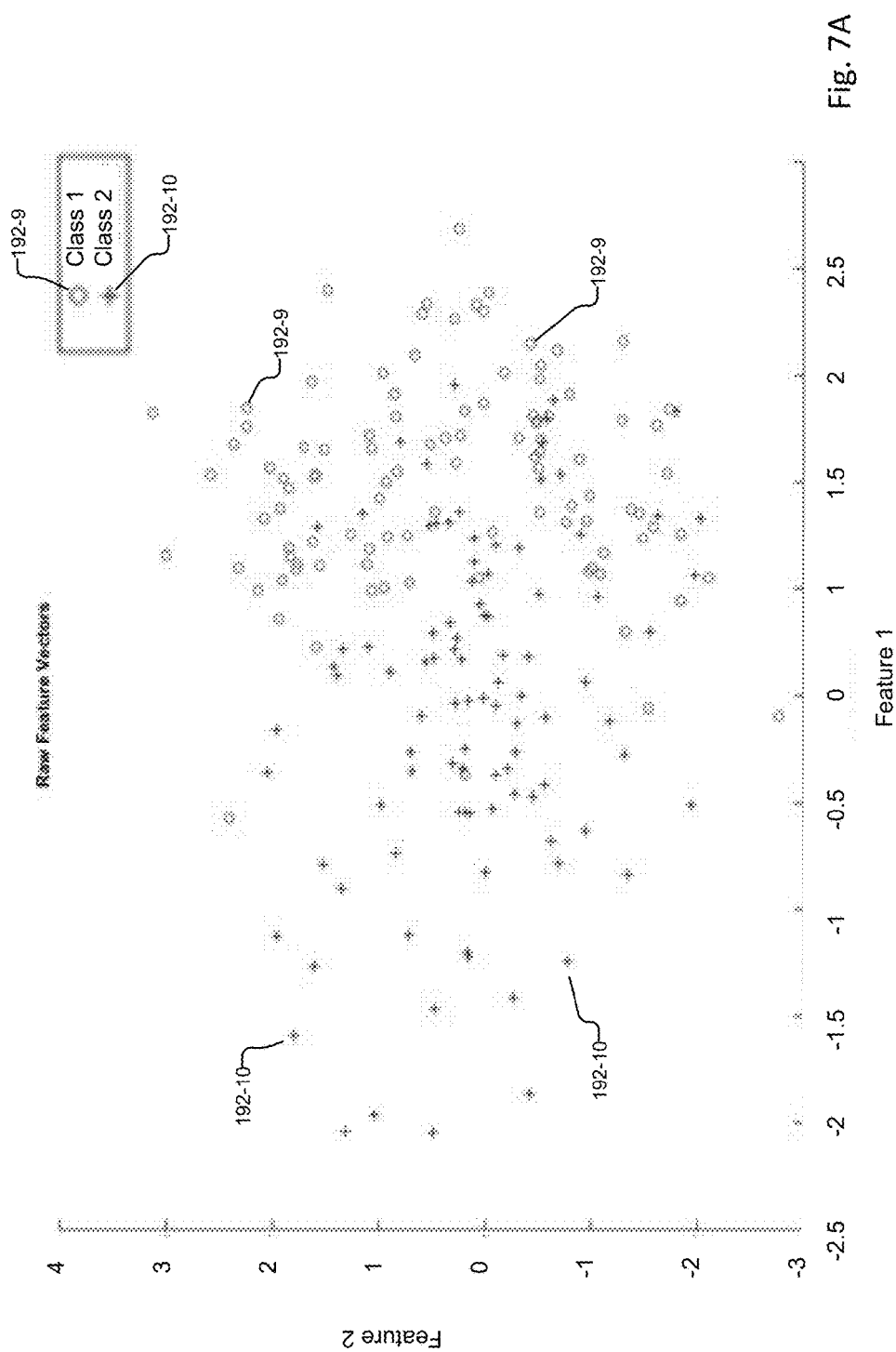
FIG. 7A shows an exemplary scatter plot of feature vectors corresponding to two different classes of minerals within a sample.

FIG. 7A shows an exemplary scatter plot of feature vectors 192-9 and 192-10 corresponding to two different classes of minerals within a sample 114. In the example, the sample 114 includes two types or classes of minerals. Also in the example, feature vectors 192-9 and 192-10 are associated with two distinct features of the sample 114. Feature vectors 192-9 associated with a first class of minerals or "Class 1" are represented as circles in the scatter plot, and feature vectors 192-10 associated with a second class of minerals or "Class 2" are represented as crosses (+) in the scatter plot.

Figure 7B:
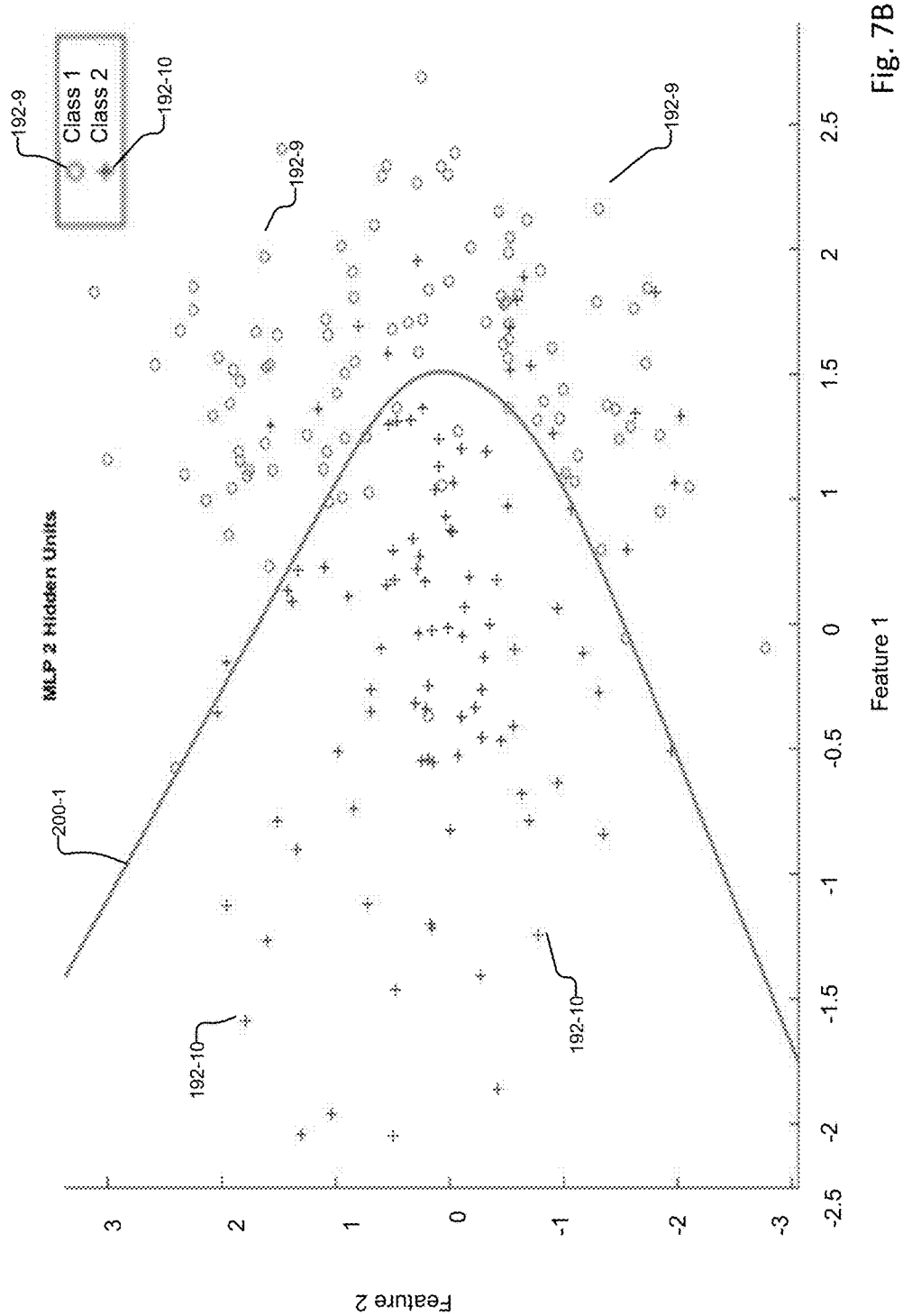
FIGS. 7B and 7C show the same exemplary scatter plot of feature vectors as shown in FIG. 7A, with FIG. 7B additionally showing the results of applying a low-dimensional Multilayer Perceptron (MLP) machine learning training algorithm to the plot of FIG. 7A and with FIG. 7C additionally showing the results of applying a high-dimensional Multilayer Perceptron (MLP) machine learning training algorithm to the plot of FIG. 7A for constructing segmented mineralogy.

FIG. 7B shows the results of applying a low-dimensional Multilayer Perceptron (MLP) machine learning training algorithm 196-2 to the plot of FIG. 7A for constructing segmented image representations of the sample 136/146/156. In the example, two MLP hidden units, or hidden layer neurons, are selected to accomplish the low-dimensional MLP 196-2 processing.

In response to the machine learning engine 172 applying the low-dimensional MLP machine learning training algorithm 196-2 to the feature vectors 192 of FIG. 7A, a decision surface or boundary 200-1 is defined among the feature vectors for constructing a segmented image representation of the sample 114. In the example, feature vectors 192 that fall to the left of the decision boundary 200-1 are statistically determined to belong to the "Class 1" class of minerals. Feature vectors 192 located further away to the left of the decision boundary 200-1 have a higher probability of belonging to Class 1 than feature vectors located nearer the decision boundary 200-1. In a similar vein, features having feature vectors 192 that fall to the right of the decision boundary 200-1 are determined to belong to the "Class 2" class of minerals. Feature vectors 192 located further away to the right of the decision boundary 200-1 have a higher probability of belonging to Class 2 than feature vectors located nearer the decision boundary 200-1.

Within the scatter plot of FIG. 7B, a perfect image segmentation algorithm would optimally generate a decision boundary 200-1 such that all circle data points for feature vectors 192-9 would be located to right of the decision boundary 200-1, and all cross data points for feature vectors 192-10 would be located to the left of the decision boundary 200-1, in one example. Features having feature vectors that fall on the decision boundary 200-1 belong to both classes with 50% probability.

Figure 7C:
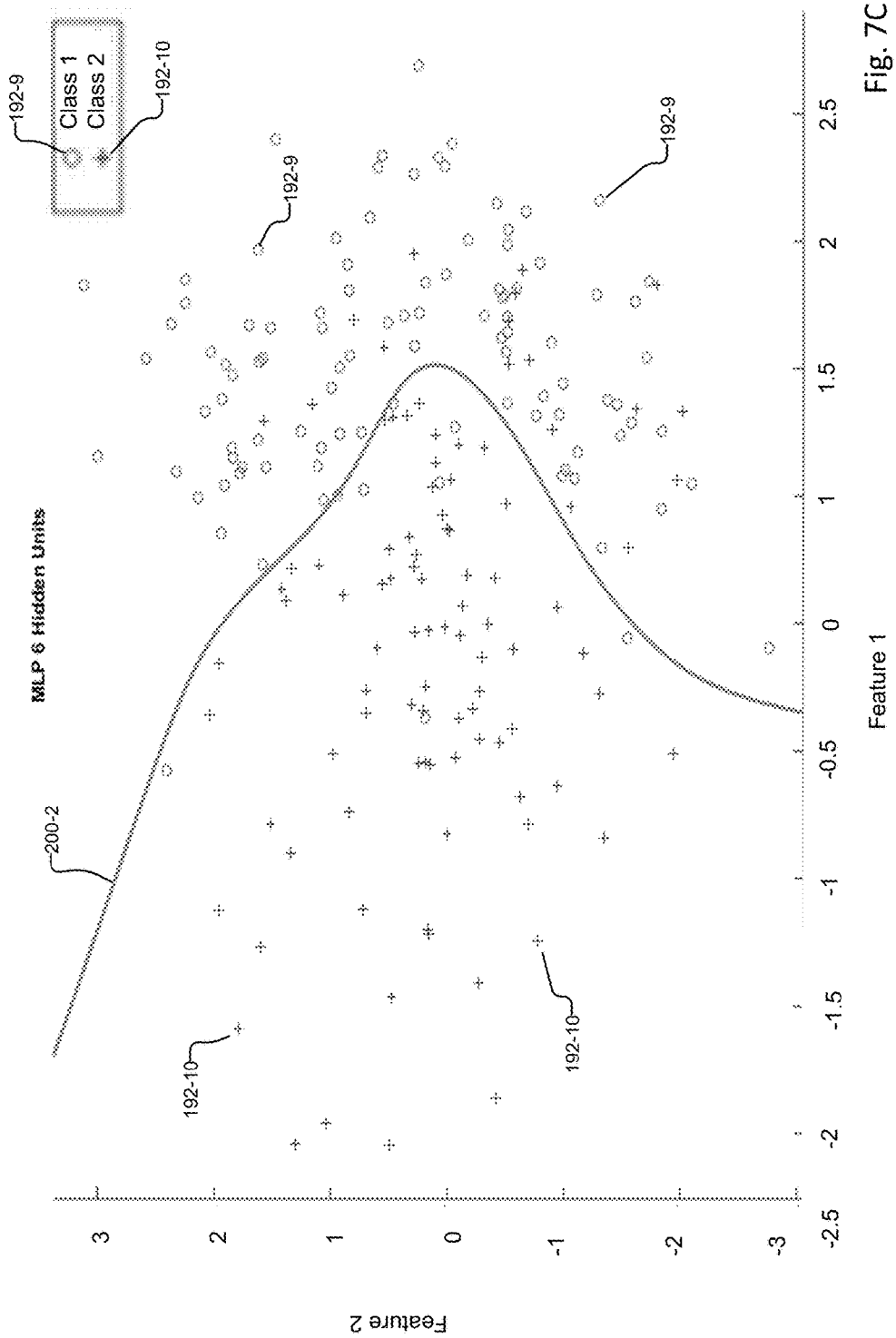

FIG. 7C shows the results of applying a high-dimensional Multilayer Perceptron (MLP) machine learning training algorithm to the plot of FIG. 7A. In the example, six MLP hidden units are selected to accomplish the high-dimensional MLP 196-2 processing. In response to the machine learning engine 172 applying the high-dimensional MLP machine learning training algorithm 196-2 to the feature vectors of FIG. 7A, a decision surface or boundary 200-2 is defined among the feature vectors 192-9 and 192-10 for constructing a segmented image representation of the sample 114.

While this invention has been particularly shown and described with references to preferred embodiments thereof, it will be understood by those skilled in the art that various changes in form and details may be made therein without departing from the scope of the invention encompassed by the appended claims.

What is claimed is:

1. A mineralogy segmentation method for a multimodality imaging system, the method comprising:
   generating one or more image datasets of a sample;
   creating one or more two dimensional mineral maps covering at least part of the one or more image datasets using energy dispersive x-ray spectroscopy to identify the minerals within the sample;
   applying the one or more two dimensional mineral maps to the one or more image datasets to identify and label regions in the image datasets associated with minerals within the sample;
   extracting feature vectors from the labeled regions by extracting texture and edges via feature generators including filters that extract the texture and edges;
   executing machine learning training algorithms upon the extracted feature vectors to learn behavior information of the feature vectors; and
   applying the behavior information learned from the machine learning training algorithms to the labeled one or more image datasets to construct a segmented image representation of the sample that classifies the minerals within the sample.

2. The method of claim 1, wherein extracting feature vectors from the labeled regions via feature generators comprises a feature extraction engine executing upon a computer system that uses the feature generators to extract the feature vectors.

3. The method of claim 2, wherein the feature generators include a Gabor filter.

4. The method of claim 1, wherein executing machine learning training algorithms upon the extracted feature vectors comprises a machine learning engine executing upon a computer system that accepts the extracted feature vectors passed by the feature extraction engine; and executes the machine learning training algorithms upon the extracted feature vectors.

5. The method of claim 1, wherein the machine learning training algorithms include a Random Forest machine learning training algorithm.

6. The method of claim 1, wherein generating one or more image datasets of the sample comprises generating one or more x-ray volume datasets of the sample as the one or more image datasets.

7. The method of claim 6, further comprising generating the one or more x-ray volume datasets of the sample using different x-ray energies.

8. The method of claim 1, wherein applying the one or more mineral maps to the one or more image datasets comprises using the one or more mineral maps to identify and label regions associated with the minerals within the sample.

9. The method of claim 1, wherein at least one of the image datasets is an x-ray volume dataset and the segmented image representation of the sample is a segmented x-ray volume dataset.

10. The method of claim 1, wherein generating one or more image datasets of the sample comprises generating one or more FIB-SEM volume datasets of the sample as one or more image datasets using a focused ion beam scanning electron microscope (FIB-SEM) imaging and analysis system of the multi-modality imaging system.

11. The method of claim 10, further comprising generating the one or more FIB-SEM volume datasets of the sample using backscattered electron and/or secondary electron modes of the FIB-SEM imaging and analysis system.

12. The method of claim 1, wherein at least one of the image datasets is a FIB-SEM volume dataset and the segmented image representation of the sample is a segmented FIB-SEM volume dataset.

13. The method of claim 1, wherein generating one or more image datasets of the sample comprises generating one or more FIB-SEM datasets of the sample as one or more image datasets using a focused ion beam scanning electron microscope (FIB-SEM) imaging and analysis system of the multimodality imaging system.

14. The method of claim 13, further comprising generating the one or more 2D images of the sample using backscattered electron and/or secondary electron modes of the FIB-SEM imaging and analysis system.

15. A multimodality imaging system for segmenting minerals of a sample, the system comprising:
an imaging system generating one or more image datasets of the sample;
an energy dispersive x-ray spectroscopy system creating one or more two dimensional mineral maps that identify the minerals within the sample using energy dispersive x-ray spectroscopy to identify the minerals within the sample; and
a computer system that applies the one or more two dimensional mineral maps to the one or more image datasets to identify and label regions in the one or more image datasets associated with the minerals within the sample, that utilizes a feature extraction engine that extracts feature vectors including texture from the labeled regions, that utilizes a machine learning engine that executes machine learning training algorithms upon the extracted feature vectors to learn behavior information of the feature vectors, and that applies the behavior information learned from the machine learning training algorithms to the one or more image datasets to construct a segmented image representation of the sample that classifies the minerals within the sample.

16. The system of claim 15, wherein the imaging system generates one or more x-ray volume datasets of the sample as the image datasets of the sample.

17. The system of claim 15, wherein the imaging system includes a focused ion beam scanning electron microscope (FIB-SEM) imaging system that generates one or more FIB-SEM volume datasets of the sample as the image datasets of the sample.

18. The system of claim 15, wherein the imaging system includes a focused ion beam scanning electron microscope (FIB-SEM) that generates one or more 2D images of the sample as the image datasets of the sample.

19. A mineralogy segmentation method for a multimodality imaging system, the method comprising:
generating one or more image datasets of a sample;
creating one or more two dimensional mineral maps covering at least part of the one or more image datasets using energy dispersive x-ray spectroscopy to identify the minerals within the sample;
applying the one or more two dimensional mineral maps to the one or more image datasets to identify and label regions in the image datasets associated with minerals within the sample;
extracting feature vectors from the labeled regions by extracting texture and edges via feature generators including filters that extract the texture; and
using the feature vectors to construct a segmented image representation of the sample that classifies the minerals within the sample.

20. The method of claim 19, further comprising assigning mineralogy at every pixel for selected slices of the datasets.

21. The method of claim 19, further comprising wherein the feature vectors are provided for each pixel.

* * * * *